US00PP07764P

United States Patent [19]

VandenBerg

[11] Patent Number: Plant 7,764

[45] Date of Patent: Jan. 7, 1992

[54] CHRYSANTHEMUM PLANT NAMED EUREKA

[75] Inventor: Cornelis P. VandenBerg, Salinas, Calif.

[73] Assignee: Yoder Brothers, Inc., Barberton, Ohio

[21] Appl. No.: 570,876

[22] Filed: Aug. 21, 1990

[51] Int. Cl.[5] ..... A01H 5/00

[52] U.S. Cl. ..... Plt./74

[58] Field of Search ..... Plt./74, 82.2

*Primary Examiner*—Howard J. Locker

*Attorney, Agent, or Firm*—Foley & Lardner

[57] ABSTRACT

A Chrysanthemum plant named Eureka particularly characterized by its flat capitulum form; spooned anemone capitulum type with a small anemone cushion; yellow ray floret color; diameter across face of capitulum of 51 to 57 mm. when fully opened when grown as a pinched spray pot mum; photoperiodic response to short days of 50 to 56 days; plant height of 18 to 33 cm. when grown as a pinched pot mum; and semi-spreading branching pattern, with 4 to 5 breaks per plant after pinch.

3 Drawing Sheets

1

The present invention comprises a new and distinct cultivar of Chrysanthemum, botanically known as *Dendranthema grandiflora*, and referred to by the cultivar name Eureka.

Eureka, identified as 86-408002, was originated from a cross made by Cornelis P. VandenBerg in a controlled breeding program in Salinas, Calif., in 1985.

The female parent of Eureka was the cultivar Rejoice, disclosed in U.S. Plant Pat. No. 5,779. Certain of the principal characteristics of Rejoice are set forth in attached Chart A which compares Eureka with its female parent Rejoice.

The male parent of Eureka was the cultivar Tan, disclosed in U.S. Plant Pat. No. 5,619. Tan can be described as a bronze-orange flat daisy spray pot mum having a flowering response to short days of 50 to 55 days under normal conditions, a plant height of 23 to 30 cm. with 15 to 18 long days after the sticking of unrooted cuttings and 1 to 3 applications of 2500 ppm B-9 SP, a semi-spreading breaking action with 4 to 5 breaks per plant after pinch, and a diameter of capitulum of 62 to 70 mm.

Eureka was discovered and selected as one flowering plant within the progeny of the stated cross by Cornelius P. VandenBerg in July 1986, in a controlled environment in Salinas, Calif.

The first act of asexual reproduction of Eureka was accomplished when vegetative cuttings were taken from the initial selection in September 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Eureka are firmly fixed and are retained through successive generations of asexual reproduction.

Eureka has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice.

2

The following traits have been repeatedly observed and are determined to be basic characteristics of Eureka, which, in combination, distinguish this Chrysanthemum as a new and distinct cultivar:

1. Flat capitulum form.
2. Spooned anemone capitulum type with a small anemone cushion.
3. Yellow ray floret color.
4. Diameter across face of capitulum of 51 to 57 mm. when fully opened, when grown as a pinched spray pot mum.
5. Photoperiodic flowering response to short days of 50 to 56 days.
6. Plant height, with 15 long days after sticking of unrooted cuttings, and with 1 to 2 applications of 2500 ppm B-9 SP, ranges from 18 to 33 cm. when grown as a pinched pot mum with 4 cuttings in a 15 cm. pot.
7. Branching pattern is semi-spreading, with each plant having 4 to 5 laterals after pinch.

The accompanying photographic drawings show typical inflorescence and leaf characteristics of Eureka, with the colors being as nearly true as possible with illustrations of this type.

Sheet 1 is a color photograph of Eureka grown as a pinched spray pot mum with 4 cuttings in a 15 cm. pot.

Sheet 2 is a black and white photograph of three views of the influrescence of Eureka.

Sheet 3 is a black and white photograph showing the upper and under sides of the leaves of Eureka at three stages of development (mature, intermediate and immature).

In Sheets 2 and 3 a measuring tape in centimeters has been added.

Of the commercial cultviars known to the inventors, the most similar in comparison to Eureka is the female parent Rejoice. Reference is made to attached Chart A, which compares certain characteristics of Eureak to the same characteristics of Rejoice.

Similar traits are capitulum form, flowering response to short days, and branching pattern. The ray floret color of Eureka is a deeper yellow than that of Rejoice, and Eureka has a smaller diameter of capitulum than Rejoice. Eureka has a faster growth rate than Rejoice and is given two long day weeks after sticking unrooted cuttings prior to start of short days, while Rejoice is given three long day weeks. Therefore, the plant heights are not directly comparable. In addition, Rejoice has often shown foliar spotting and flecking, a very undesirable trait, while Eureka has not shown this foliar defect in trails at Salinas, Calif.

When compared with both parents, Eureka has a smaller diameter of capitulum than both parents. The ray florets of Eureka are spooned, while both parents have flat, straight ray florets.

In the following description color references are made to The Royal Horticultural Society Colour Chart. The color values were determined on plant material grown as a pinched spray pot mum in Salinas, Calif., on May 2, 1990.

Classification:

*Botanical.*—*Dendranthema grandiflora* cv Eureka.

*Commercial.*—Spooned anemone spray pot mum.

INFLORESCENCE

A. Capitulum:

*Form.*—Flat.

*Type.*—Spooned anemone, with small anemone cushion.

*Diameter across face.*—51 to 57 mm. when fully opened, with anemone cushion approximately 15 mm.

B. Corolla of ray florets:

*Color (general tonality from a distance of three meters).*—Yellow.

*Color (upper surface).*—9A.

*Color (under surface).*—9B.

*Shape.*—Spooned, with irregular length of spoons.

C. Corolla of disc Florets:

*Color (mature).*—14B.

*Color (immature).*—14B, overlaid with 144B.

D. Reproductive organs:

*Androecium.*—Present on disc florets only; moderate pollen.

*Gynoceium.*—Present on both ray and disc florets.

PLANT

A. General Appearance:

*Height.*—18 to 33 cm. when grown as a pinched pot mum in a 15 cm. pot with 15 long days after direct sticking of unrotted cuttings and 1 to 2 applications of 2500 ppm B-9 SP.

*Branching pattern.*—Semi-spreading, with 4 to 5 laterals after pinch.

B. Foliage:

*Color (upper surface).*—147A.

*Color (under surface)*—147B.

*Shape.*—See photograph.

CHART A

COMPARISON OF EUREKA AND REJOICE

| CHARACTERISTIC | EUREKA | REJOICE |
|---|---|---|
| Ray floret color | Yellow | Yellow |
| Capitulum form and type | Flat spooned anemone | Flat anemone |
| Diameter across face of capitulum | 51 to 57 mm. | 70 to 75 mm. |
| Flowering response | 50 to 56 days | 49 to 56 days |
| Plant height: | 18 to 33 cm. with 15 long days | 23 to 38 cm. with 22 long days |
| Branching pattern | Semi-spreading 4 to 5 laterals | Semi-spreading 4 to 5 laterals |

COMPARISONS MADE OF PLANTS GROWN AS PINCHED SPRAY POT MUMS IN SALINAS, CALIFORNIA

I claim:

1. A new and distinct Chrysanthemum plant named Eureka, as described and illustrated.

* * * * *

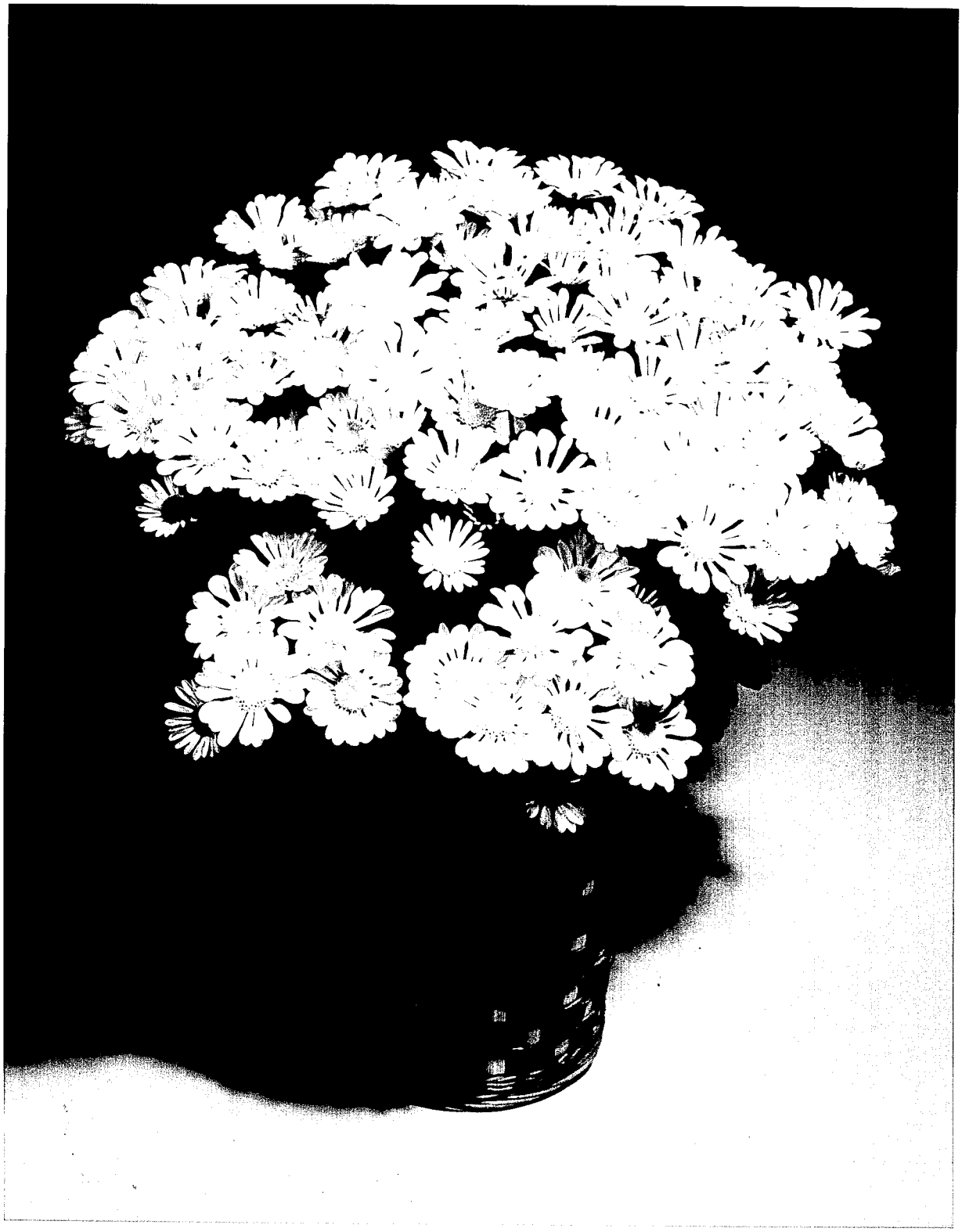

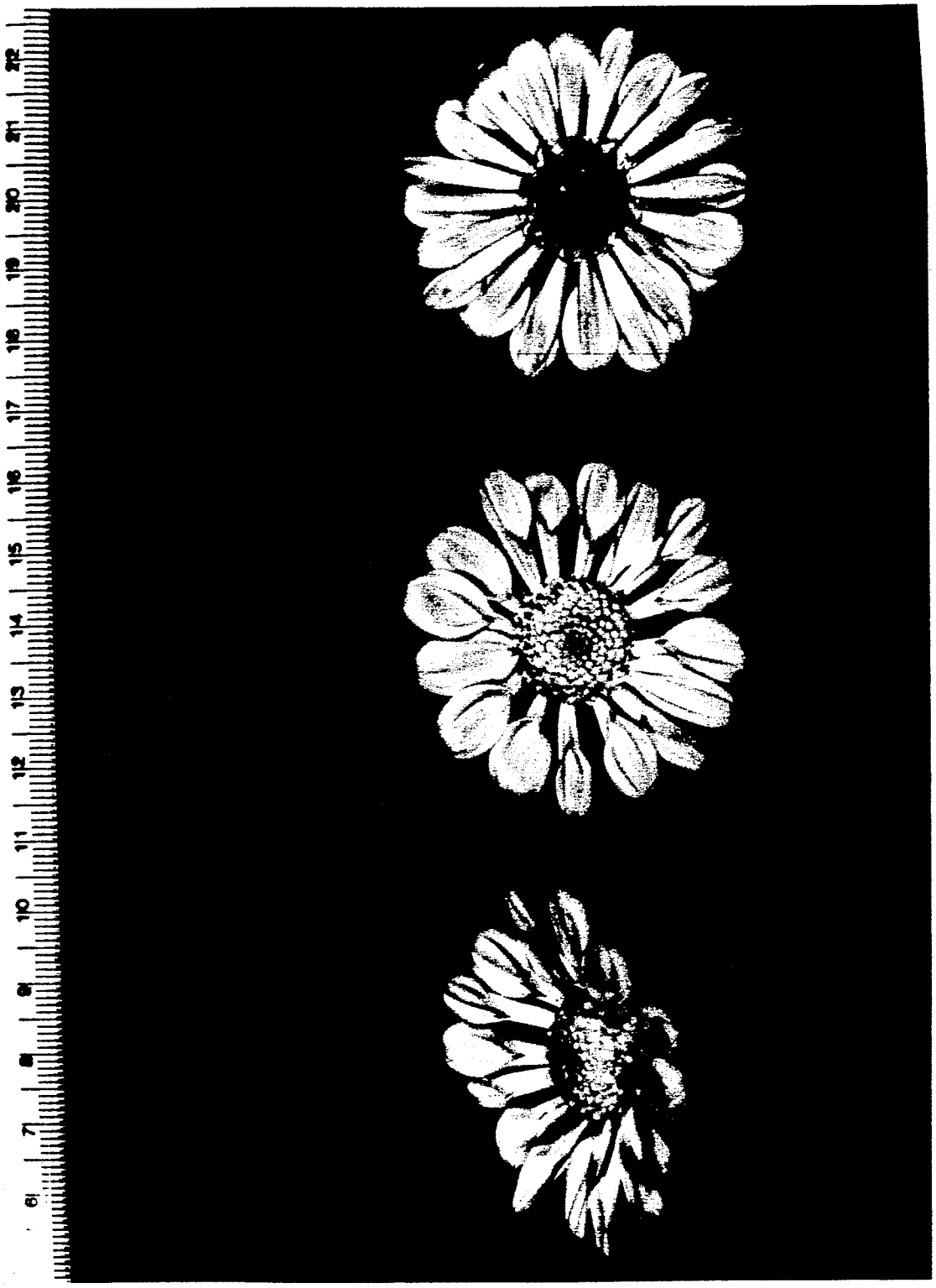

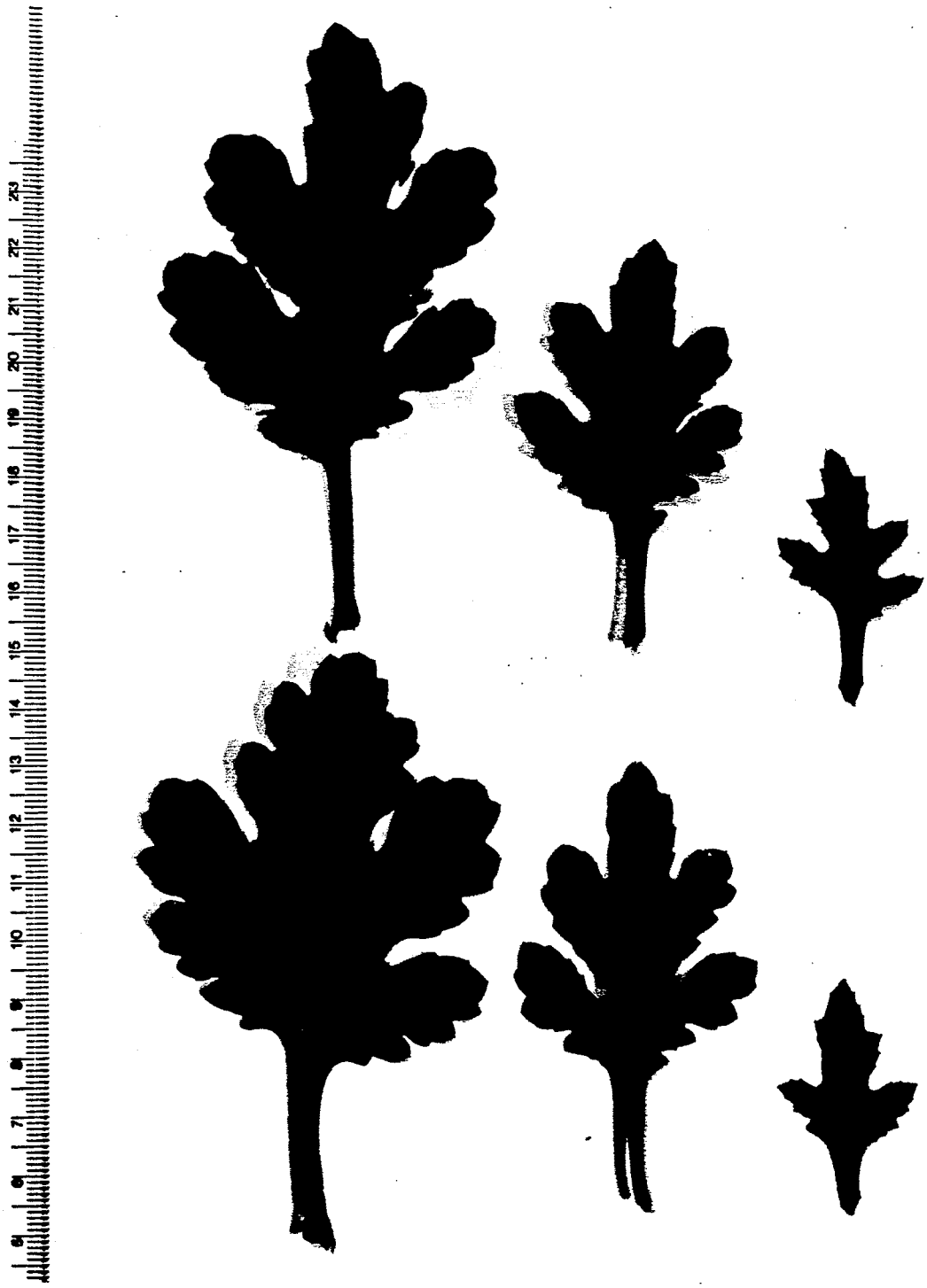

UNITED STATES PATENT AND TRADEMARK OFFICE

CERTIFICATE OF CORRECTION

PATENT NO. : PP 7,764

DATED : January 7, 1992

INVENTOR(S) : Cornelis P. VandenBerg

It is certified that error appears in the above-identified patent and that said Letters Patent is hereby corrected as shown below:

Column 1, line 26, "Cornelius" should read --Cornelis--.

Column 2, line 37, "Eureak" should read --Eureka--.

Column 3, line 5, "trails" should read --trials---.

Column 4, line 12, "unrotted" should read --unrooted--.

Sheet 2 of 3 of Drawings, "Jan. 7, 1991" (the date of patent) should read --Jan. 7, 1992--.

Sheet 3 of 3 of Drawings, "Jan. 7, 1991" (the date of patent) should read --Jan. 7, 1992--.

Signed and Sealed this

Seventh Day of December, 1993

Bruce Lehman

*Attest:*

BRUCE LEHMAN

*Attesting Officer*

*Commissioner of Patents and Trademarks*